US00PP21188P2

(12) United States Plant Patent
van Kleinwee

(10) Patent No.: US PP21,188 P2
(45) Date of Patent: Aug. 10, 2010

(54) ***PELARGONIUM* PLANT NAMED 'ZONFIWIT'**

(50) Latin Name: *Pelargonium×hortorum*
Varietal Denomination: Zonfiwit

(75) Inventor: Theodorus Cornelis Maria van Kleinwee, Zwaag (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/460,015

(22) Filed: Jul. 10, 2009

(51) Int. Cl.
*A01H 5/00* (2006.01)

(52) U.S. Cl. ..... Plt./326

(58) Field of Classification Search ..... Plt./326
See application file for complete search history.

*Primary Examiner*—Kent L Bell
(74) *Attorney, Agent, or Firm*—S. Matthew Edwards

(57) ABSTRACT

A new *Pelargonium* plant named 'Zonfiwit', particularly distinguished by the large, round, semi-double pure white flowers, inflorescences held nicely above the foliage, dark green foliage nearly without zonation, medium vigor, and fairly tight mounding plant habit.

1 Drawing Sheet

Latin name of the genus and species of the plant claimed: *Pelargonium×hortorum.*

Varietal denomination: 'Zonfiwit'.

BACKGROUND OF THE NEW PLANT

The present invention comprises a new zonal *geranium*, botanically known as *Pelargonium×hortorum* and hereinafter referred to by the variety name 'Zonfiwit'.

'Zonfiwit' is a product of a planned breeding program. The new cultivar has large, round, semi-double, pure white flowers, inflorescences held nicely above the foliage, dark green foliage nearly without zonation, medium vigor, and fairly tight mounding plant habit.

'Zonfiwit' originates from a hybridization made in May 2003 in a controlled breeding program in Enkhuizen, The Netherlands. The female parent was the commercial variety 'Fisrowi,' U.S. Plant Pat. No. 12,389, having white flower color and medium green foliage.

The male parent of 'Zonfiwit' was the unpatented variety 'Klesail', with white-flowers, shorter peduncles, dark-green foliage but less intense, and more compact habit.

'Zonfiwit' was selected as one flowering plant within the progeny of the stated cross in May 2004 in a controlled environment in Enkhuizen, The Netherlands.

The first act of asexual reproduction of 'Zonfiwit' was accomplished when vegetative cuttings were propagated from the initial selection in August 2004 in a controlled environment in Enkhuizen, The Netherlands.

BRIEF SUMMARY OF INVENTION

Horticultural examination of plants grown from cuttings of the plant initiated in August 2004 in Enkhuizen, The Netherlands, and continuing thereafter, has demonstrated that the combination of characteristics as herein disclosed for 'Zonfiwit' are firmly fixed and are retained through successive generations of asexual reproduction.

'Zonfiwit' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Pelargonium* as a new and distinct variety.

A Plant Breeder's Right for this cultivar was applied for in Switzerland in June 2009. 'Zonfiwit' has not been made publicly available more than one year prior to the filing of this application.

BRIEF DESCRIPTION OF THE PHTOGRAPHS

The accompanying photographic drawing shows typical flower and foliage characteristics of 'Zonfiwit' with colors being as true as possible with an illustration of this type. The photographic drawing shows a flowering potted plant of the new variety and a close-up of the flowers.

DETAILED BOTANICAL DESCRIPTION

The measurements were taken in Hillscheid, Germany in late April 2009 on plants that were growing on benches in a greenhouse. Culture of these plants started around mid February 2009, when rooted cuttings were planted into 12 cm pots and grown out in the greenhouse. At the time of measurements, the plants were 10 weeks old (from potting of rooted cuttings). Temperature in the greenhouse ranged from 14° C. to 16° C.

Color references are made to The Royal Horticultural Society Colour Chart (R.H.S.) 2001.

TABLE 1

DIFFERENCES BETWEEN THE NEW VARIETY 'ZONFIWIT' AND A SIMILAR VARIETY

| | 'Zonfiwit' | 'Fistablanc' (U.S. Plant Pat. No. 13,186) |
|---|---|---|
| Flower shape: | More uniform, rounder | Less uniform and less round |
| Peduncle length: | Slightly shorter | Longer |
| Foliage color: | More intense green | Less intense green |
| Plant habit: | More compact, tighter canopy | Less compact, more open canopy |

Plant:
- *Form, growth and habit.*—Medium in size, compact habit, fair branching.
- *Plant height.*—14.8 cm.
- *Plant height (inflorescence included).*—20-24 cm.
- *Plant width.*—24.2 cm.
- *Number of branches.*—4-5.

Foliage:
- *Immature leaf, color upper surface.*—RHS 137B to RHS 137C.
- *Immature leaf, color lower surface.*—RHS 137C to RHS 137D.
- *Mature leaf, color upper surface.*—RHS 137A.
- *Mature leaf, color lower surface.*—RHS 137C.
- *Length.*—5.3-6.0 cm.
- *Width.*—9.2 cm.
- *Shape.*—Kidney-shaped to round.
- *Base shape.*—Cordate, with a gap between the lowest lobes.
- *Apex shape.*—Rounded, very slightly lobed.
- *Margin.*—Bi-crenate.
- *Texture, upper surface.*—Velvety with very short pubescence.
- *Lower surface.*—Short pubescence, especially along the protruding veins.
- *Leaf zonation.*—Very weak, usually visible on young leaves only, RHS 147A.
- *Leaf zonation width.*—Approximately 1-1.5 cm.
- *Color of veins, upper surface.*—Closest to RHS 137D but almost indistinct.
- *Color of veins, lower surface.*—RHS 144B.
- *Petiole color.*—RHS 137D on the upper side, RHS 143C on the lower side.
- *Petiole length.*—5-8 cm.
- *Diameter of petiole.*—0.2-0.3 cm.
- *Texture.*—Densely covered with short hairs.

Stem:
- *Color of stem.*—RHS 143B.
- *Length of stem.*—9-13 cm.
- *Diameter at midpoint.*—0.7-0.8 cm.
- *Length of internodes.*—0.5-2.0 cm.
- *Texture.*—Dense pubescence, very short hair.

Inflorescence:
- *Type.*—Umbel, semi-spherically shaped.
- *Duration of flowering.*—Continuously throughout the Summer months.
- *Lastingness of individual flowers.*—About 5-7 days.
- *Average quantity of inflorescences per plant.*—4.
- *Average number of flowers and buds per inflorescence.*—About 35-45.
- *Umbel diameter.*—10-10.5 cm.
- *Umbel depth.*—About 6.0 cm.
- *Color of peduncle.*—RHS 143 B.
- *Length of peduncle.*—13-17 cm.
- *Peduncle diameter.*—0.3-0.4 cm.
- *Texture.*—Densely covered with very short hair.
- *Color of pedicel.*—RHS 143A to RHS143B.
- *Length of pedicel.*—3.3-3.7 cm.
- *Diameter of pedicel.*—0.1 cm.
- *Texture.*—Densely covered with glandular hair.

Corolla:
- *Form.*—Semi-double, nearly round and weakly cup-shaped to nearly flat.
- *Diameter of flower.*—5.4-5.6 cm.
- *Vertical diameter (depth) of flower.*—1.0-1.3 cm.
- *Number of petals.*—Most often 7-8.
- *Color upper petals, upper surface.*—Whiter than RHS 155D.
- *Color upper petals, lower surface.*—Mainly whiter than RHS 155D, partly a shade of RHS 150D or RHS 157D may occur.
- *Length of upper petals.*—2.8-3.2 cm.
- *Width of upper petals.*—2.2-2.5 cm.
- *Color lower petals, upper surface.*—Whiter than RHS 155D.
- *Color lower petals, lower surface.*—RHS 155D, may appear very slightly greenish, RHS 157D, in parts.
- *Length of lower petals.*—2.7-2.9 cm.
- *Width of lower petals.*—2.3-2.5 cm.
- *Petal shape.*—Obovate.
- *Apex shape.*—Rounded.
- *Margin.*—Entire, apex may appear weakly crenulate.
- *Petal texture.*—Smooth, glabrous.
- *Color petaloids.*—Whiter than RHS 155D.
- *Number of petaloids.*—0-2.
- *Length of petaloids.*—1-1.5 cm; can be quite variable.
- *Width of petaloids.*—0.4-1.0 cm; can be quite variable.

Bud (just before opening):
- *Color.*—RHS 155A to RHS 150D.
- *Length.*—1.6-1.8 cm.
- *Width.*—1.1-1.3 cm.
- *Shape.*—Elliptic.

Calyx:
- *Number of sepals.*—5.
- *Color of sepals, upper surface (inner).*—RHS 143C.
- *Lower surface (visible).*—RHS 143A to RHS 143B.
- *Length of sepals.*—0.9-1.0 cm.
- *Width of sepals.*—0.3-0.4 cm for the largest sepal, 0.2-0.3 cm for the others.
- *Sepal shape.*—Lanceolate.
- *Apex shape.*—Acute.
- *Margins.*—Entire.
- *Texture, upper surface (inner).*—Glabrous.
- *Lower surface (visible).*—Densely covered with short glandular hair and additional soft longer hair.

Reproductive organs:
- *Pistil.*—One.
- *Length.*—1.0 cm.
- *Style color.*—RHS 150D.
- *Style length.*—0.4 cm.
- *Stigma color.*—RHS 157D.
- *Ovary color.*—RHS 138A.
- *Number of anthers.*—Most often 7.
- *Length of anthers.*—0.2 cm.
- *Anther color.*—RHS 32D.
- *Length filaments.*—0.6-0.8 cm.
- *Color of filaments.*—RHS 155D.
- *Pollen amount.*—Moderate (typical).
- *Color of pollen.*—RHS 25A.
- *Fertility/seed set.*—No seed set observed.

Disease/pest resistance: Disease resistance or susceptibility has not been observed on this hybrid.

What is claimed is:

1. A new and distinct variety of *Pelargonium* plant named 'Zonfiwit', substantially as illustrated and described herein.

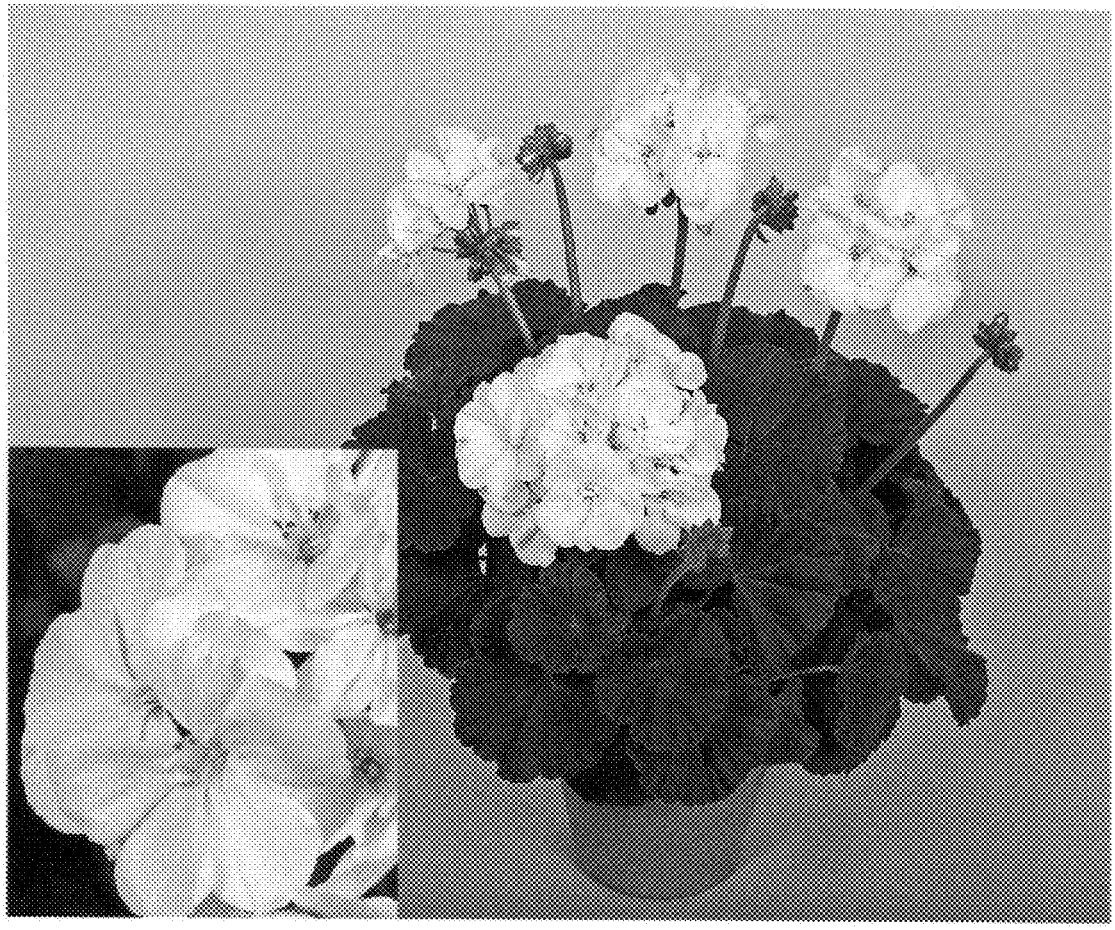

* * * * *